(12) United States Patent
Hattori

(10) Patent No.: US 11,742,085 B2
(45) Date of Patent: Aug. 29, 2023

(54) MEDICAL INFORMATION PROCESSING APPARATUS, MEDIUM, AND MEDICAL INFORMATION PROCESSING METHOD

(71) Applicant: CANON MEDICAL SYSTEMS CORPORATION, Otawara (JP)

(72) Inventor: Chihiro Hattori, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 118 days.

(21) Appl. No.: 16/872,481

(22) Filed: May 12, 2020

(65) Prior Publication Data

US 2020/0365272 A1 Nov. 19, 2020

(30) Foreign Application Priority Data

May 14, 2019 (JP) ................................ 2019-091682

(51) Int. Cl.
*G16H 50/20* (2018.01)
*G16H 10/60* (2018.01)
*G16H 50/50* (2018.01)

(52) U.S. Cl.
CPC ............. *G16H 50/20* (2018.01); *G16H 10/60* (2018.01); *G16H 50/50* (2018.01)

(58) Field of Classification Search
CPC ......... G16H 50/20; G16H 50/50; G16H 10/60
USPC ........................................................... 705/2
See application file for complete search history.

(56) References Cited

U.S. PATENT DOCUMENTS

| | | | | |
|---|---|---|---|---|
| 9,183,352 | B2* | 11/2015 | Berdyshev | G06N 5/025 |
| 10,561,321 | B2* | 2/2020 | Valys | A61B 5/7267 |
| 10,991,466 | B2* | 4/2021 | Chapman-McQuiston | |
| | | | | G16H 10/60 |
| 11,157,823 | B2* | 10/2021 | Jain | G16H 40/63 |
| 11,257,584 | B2* | 2/2022 | Buckler | G06F 16/345 |
| 2007/0208263 | A1* | 9/2007 | John | A61B 5/349 |
| | | | | 600/509 |
| 2011/0075900 | A1* | 3/2011 | Masumoto | G16H 50/30 |
| | | | | 382/128 |

FOREIGN PATENT DOCUMENTS

JP 2009-56133 A 3/2009

* cited by examiner

*Primary Examiner* — Michael Tomaszewski
*Assistant Examiner* — Rachael Sojin Stone
(74) *Attorney, Agent, or Firm* — Oblon, McClelland, Maier & Neustadt, L.L.P.

(57) ABSTRACT

A medical information processing apparatus according to an embodiment includes a processing circuitry. The processing circuitry is configured: to receive an input of first transition data indicating a transition up to the present time of a biological index value exhibiting a condition of a patient and second transition data indicating a transition up to the present time of a treatment means implemented on the patient; to set a goal value of the biological index value as a treatment index value; and to predict a time at which the biological index value of the patient will reach the treatment index value, on the basis of such first transition data and second transition data of one or more past patients different from the patient that have characteristics similar to characteristics of the first transition data and the second transition data of the patient.

12 Claims, 5 Drawing Sheets

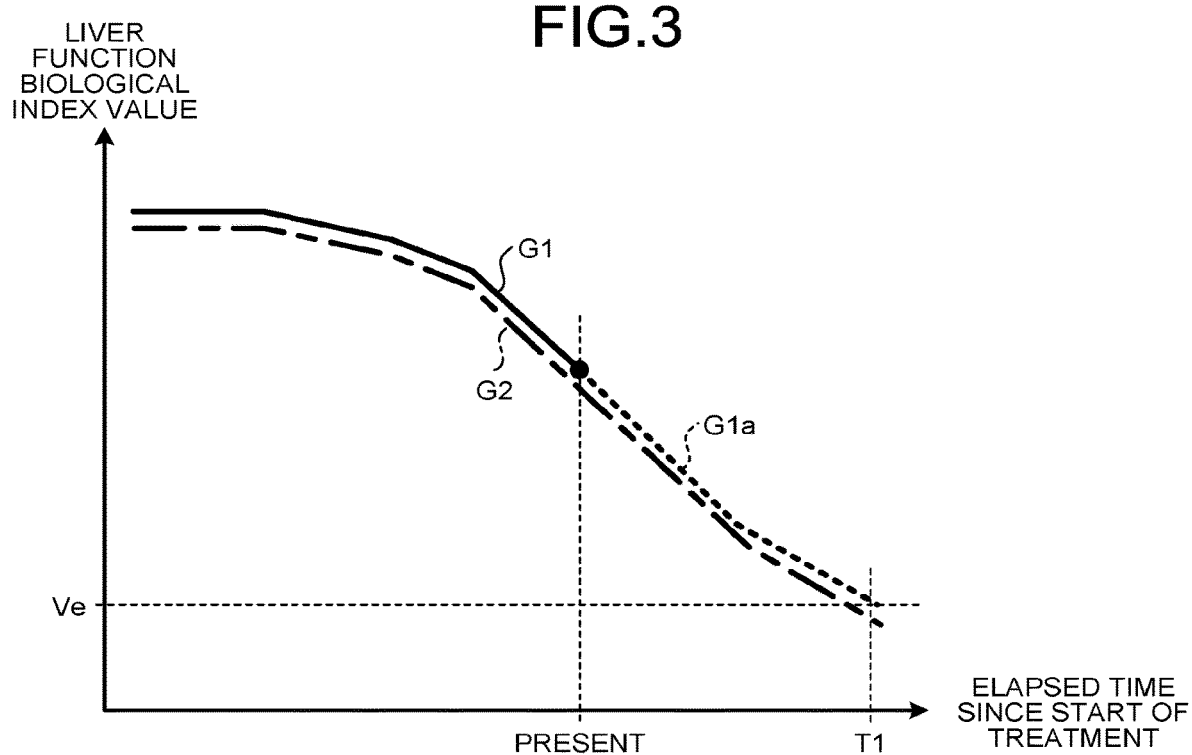
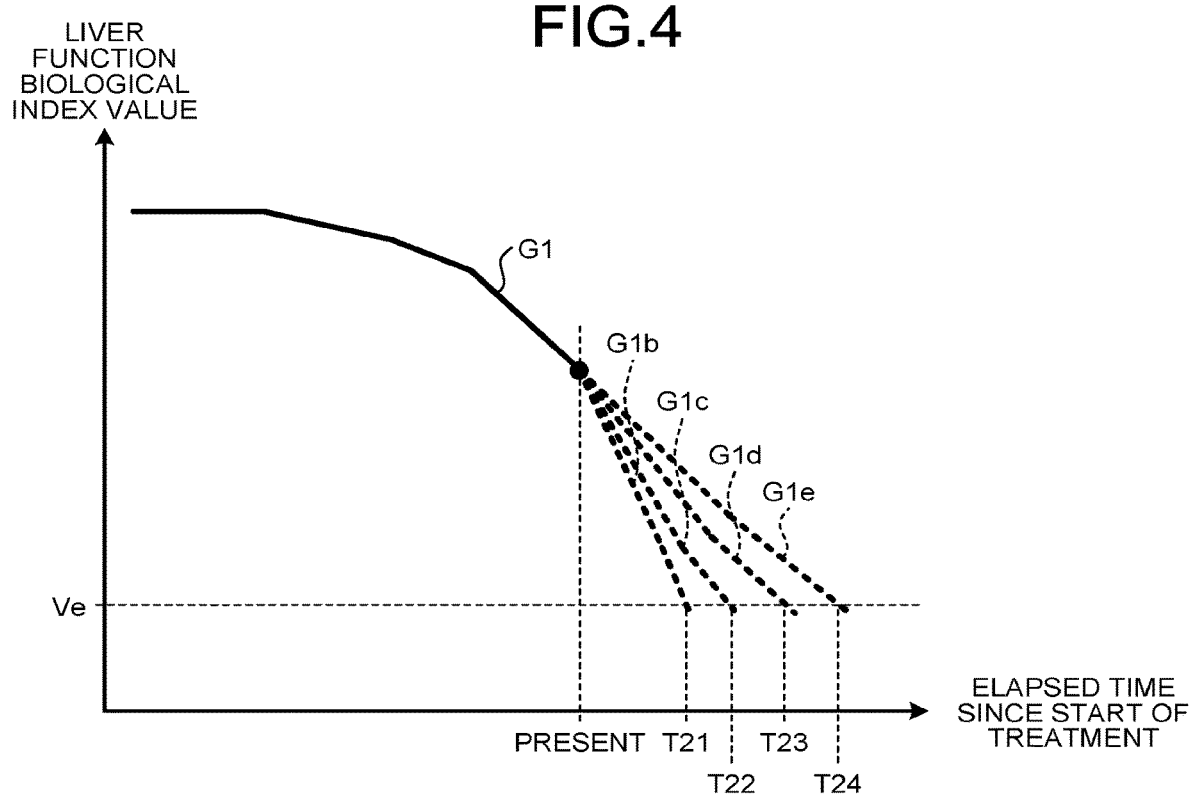

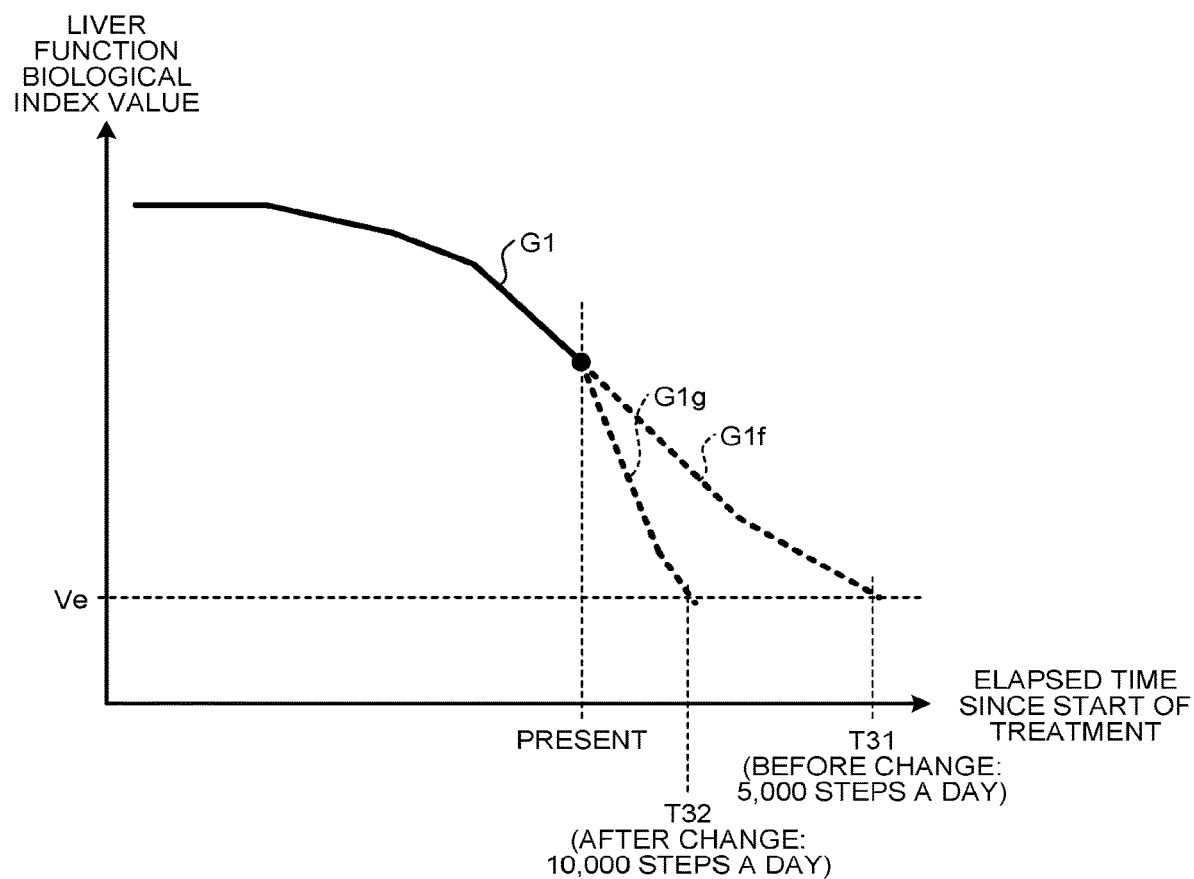

MEDICAL INFORMATION PROCESSING APPARATUS, MEDIUM, AND MEDICAL INFORMATION PROCESSING METHOD

CROSS-REFERENCE TO RELATED APPLICATIONS

This application is based upon and claims the benefit of priority from Japanese Patent Application No. 2019-091682, filed on May 14, 2019; the entire contents of which are incorporated herein by reference.

FIELD

Embodiments described herein relate generally to a medical information processing apparatus, a medium, and a medical information processing method.

BACKGROUND

Medical institutions such as hospitals treat chronic disorders occurring from various causes such as diseases, injuries, and the like. Because chronic disorders have a low possibility of exhibiting sudden changes in condition, it is common for patients to receive treatment as outpatients. Further, for disorders caused by lifestyles, the foundation of means of treatment (hereinafter, "treatment means") is formed by exercise therapy, diet therapy, and the like. Thus, how to live a daily life is an important element for the improvement of health conditions.

Further, when treatment is prolonged like the treatment for the chronic disorders and the disorders caused by lifestyles described above, some patients may find treatment or hospital visits bothersome, because it is difficult to foresee the end of the treatment and may discontinue the treatment or hospital visits at their discretion. As for the time at which treatment is to be completed, a technique has conventionally been proposed by which the time period required for the treatment of a specific disorder is predicted on the basis of an external form of the specific disorder.

The conventional technique, however, is unable to address patients having long-term treatment such as the treatment for the chronic disorders and the disorders caused by lifestyles described above. Accordingly, there is a possibility that it may be impossible to predict the time at which the treatment is to be completed.

BRIEF DESCRIPTION OF THE DRAWINGS

FIG. 3 is a drawing illustrating an example of a screen displayed by a display controlling function according to the embodiment;

FIG. 4 is a drawing illustrating another example of the screen displayed by the display controlling function according to the embodiment;

FIG. 5 is a drawing illustrating yet another example of the screen displayed by the display controlling function according to the embodiment;

DETAILED DESCRIPTION

A medical information processing apparatus according to an embodiment includes a processing circuitry. The processing circuitry is configured: to receive an input of first transition data indicating a transition up to the present time of a biological index value exhibiting a condition of a patient and second transition data indicating a transition up to the present time of a treatment means implemented on the patient; to set a goal value of the biological index value as a treatment index value; and to predict a time at which the biological index value of the patient will reach the treatment index value, on the basis of such first transition data and second transition data of one or more past patients different from the patient that have characteristics similar to characteristics of the first transition data and the second transition data of the patient.

Exemplary embodiments of a medical information processing apparatus, a medium, and a method will be explained, with reference to the accompanying drawings.

Figure 1:
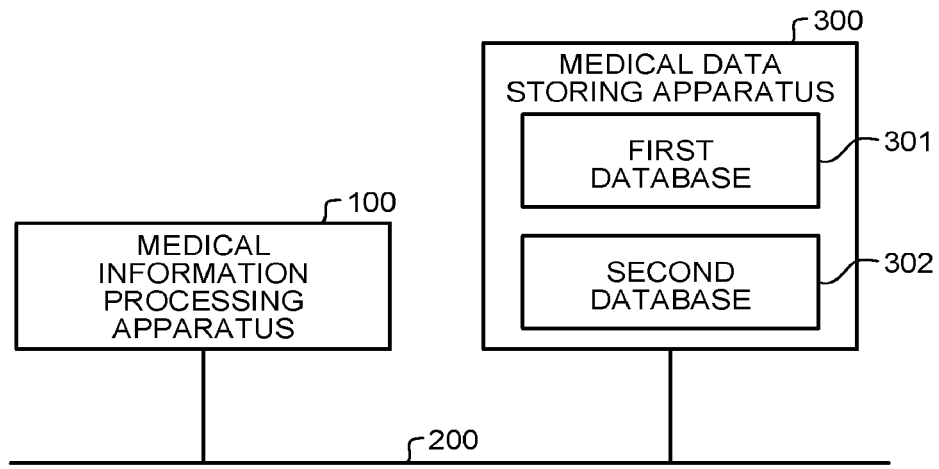
FIG. 1 is a diagram illustrating an exemplary configuration of a medical information processing system according to an embodiment.

FIG. 1 is a diagram illustrating an exemplary configuration of a medical information processing system according to an embodiment. As illustrated in FIG. 1, the medical information processing system includes a medical information processing apparatus 100 and a medical data storing apparatus 300. The medical information processing apparatus 100 is communicably connected to the medical data storing apparatus 300 via a network 200. For example, the medical information processing apparatus 100 and the medical data storing apparatus 300 are installed in a hospital or the like and are connected to each other by the network 200 realized with an intra-hospital Local Area Network (LAN) or the like.

The medical data storing apparatus 300 is configured to store therein medical data related to an examined subject (hereinafter, "patient") or the like. For example, the medical data storing apparatus 300 is realized by using a computer device such as a database server and is configured to store diagnosis/treatment data into a storage realized by using a semiconductor memory element such as a Random Access Memory (RAM) or a flash memory, or a hard disk, an optical disk, or the like.

More specifically, the medical data storing apparatus 300 stores therein: a first database 301 configured to store therein medical data of patients undergoing treatment; and a second database 302 configured to store therein medical data of patients whose treatment has been completed. In the present embodiment, a completion of treatment (synonymously, an end of treatment) is a concept including the state in which a biological index value (explained later) exhibiting conditions of a patient is in (returned to) a normal range and symptoms having completely been treated, healed, or being in remission.

The first database 301 stores therein the diagnosis/treatment data of the patients so as to be kept in correspondence with patient IDs capable of identifying the patients. For example, the diagnosis/treatment data includes: the type of disorder of each patient, first transition data indicating a transition of biological index values acquired from the patient, and second transition data indicating a transition of a treatment means for the patient.

The type of disorder indicates the name of the disease of the patient, or the like. In the present embodiment, the type of disorder primarily denotes a disorder that requires long-term treatment, such as a chronic disorder (e.g., a chronic liver or lung disorder) or a disorder caused by lifestyle. However, possible embodiments are not limited by this condition. For example, the type of disorder may denote a type of cancer or a site or a type of a bone fracture. Further, the type of disorder may denote a type of surgery or the like.

The biological index values serve as information that quantitively indicates conditions of a patient. It is possible to arbitrarily set the biological index values; however, it is desirable to select biological index values that exhibit the conditions of the disorder set as the type of disorder. For example, when the type of disorder denotes a chronic liver disorder (e.g., fatty liver), biological index values expressing liver functions such as a Low Density Lipoprotein (LDL) cholesterol value, a y-Glutamyl Transpeptidase (GTP) value, or the like may be selected. In another example, when the type of disorder denotes a chronic lung disorder, biological index values expressing pulmonary functions such as lung capacity may be selected. In yet another example, when the type of disorder denotes cancer, the size of a cancer tissue or values of a tumor marker may be used as the biological index values. In yet another example, when the type of disorder denotes a bone fracture, the thicknesses of a cartilage measured from an X-ray image or the like of a fractured part may be used as the biological index values of the patient. In yet another example, when the type of disorder denotes surgery, vital values such as the body temperatures or heart rates after the surgery, test values from a blood test, or the like may be used as the biological index values.

The first transition data is data indicating a chronological transition (changes) of the biological index values explained above. More specifically, the first transition data is expressed by sets each made up of a biological index value and date/time information indicating the time (year, month, day, time, etc.) at which the biological index value was acquired.

The treatment means denotes a physical activity carried out by the patient himself/herself or a method of treatment (a treatment plan) implemented on the patient by a medical provider such as a medical doctor, for the purpose of treatment or improving the conditions. For example, the treatment means is expressed by sets each made up of an item and a quantity of the treatment means. For example, the treatment means may define the number of steps or the duration of a walk per day. As another example, the treatment means may define the type of a drug and the amount to be administered. It is possible to arbitrarily set the treatment means; however, it is desirable to select a treatment means suitable for the disorder set as the type of disorder.

The second transition data is data indicating a chronological transition (changes) of the abovementioned treatment means. More specifically, the second transition data is expressed by sets each made up of a treatment means and date/time information indicating the time (year, month, day, time, etc.) at which the treatment means was implemented. The treatment means may be set permanently. In that situation, the second transition data records therein a treatment means of the same type and in the same quantity, from the start of the treatment to the present time. Further, when the treatment means is changed in the course of the treatment, mutually-different treatment means are recorded for before and after the change.

Further, the second database 302 stores therein first transition data and second transition data of the patients (which hereinafter may be referred to as "past patients") whose treatment has been completed. The second database 302 is generated, for example, by extracting the first transition data and the second transition data of the patients whose treatment has been completed, from the first database 301.

The data structure of the second database 302 is not particularly limited and may be in any of various forms. For example, the second database 302 may store therein the first transition data of the past patients so as to be categorized according to types of the second transition data (the treatment means) of the patients. In this data structure, for example, the second database 302 manages the first transition data of patients who underwent the treatment of walking 5,000 steps a day, separately from the first transition data of patients who underwent the treatment of walking 10,000 steps a day.

Further, in this situation, the first transition data of patients whose treatment means was changed in the course of the treatment is stored while the treatment means before and after the change is put together as one. For example, for patients whose treatment was changed from the treatment of walking 5,000 steps a day to the treatment of walking 10,000 steps a day, the first transition data is stored while being categorized in a group corresponding to the change from 5,000 steps to 10,000 steps.

Alternatively, in another data structure, the first transition data and the second transition data may be stored so as to be kept in correspondence with each of the past patients. In either of the data structures, the first transition data and the second transition data of the past patients are stored while being categorized according to the types of disorders.

The medical information processing apparatus 100 is used by medical providers such as medical doctors and is configured to perform various types of information processing processes using the medical data. For example, the medical information processing apparatus 100 is realized by using a computer device such as a workstation.

Figure 2:
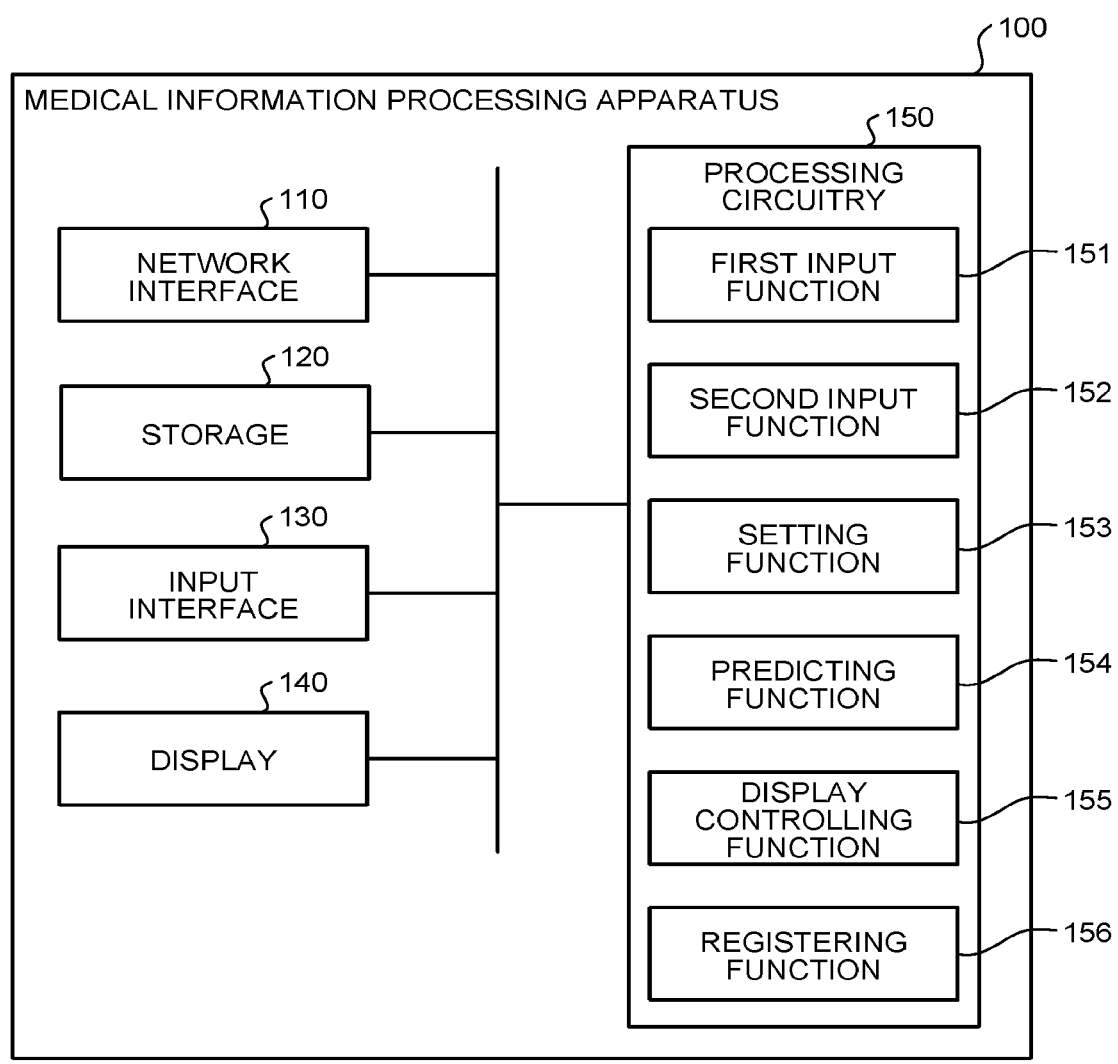
FIG. 2 is a diagram illustrating an exemplary configuration of a medical information processing apparatus according to the embodiment.

FIG. 2 is a diagram illustrating an exemplary configuration of the medical information processing apparatus 100. As illustrated in FIG. 2, the medical information processing apparatus 100 includes an network interface 110, a storage 120, an input interface 130, a display 140, and a processing circuitry 150.

The network interface 110 is connected to the processing circuitry 150 and is configured to control the transfer and communication of various types of data to and from the medical data storing apparatus 300. For example, the network interface 110 receives medical data from the medical data storing apparatus 300 and outputs the received medical data to the processing circuitry 150. For example, the network interface 110 is realized by using a network card, a network adaptor, a Network Interface Controller (NIC), or the like.

The storage 120 is connected to the processing circuitry 150 and is configured to store therein various types of data. For example, the storage 120 stores therein the first transition data and the second transition data received from the medical data storing apparatus 300. For example, the storage 120 is realized by using a semiconductor memory element such as a Random Access Memory (RAM) or a flash memory, or a hard disk, an optical disk, or the like.

The input interface 130 is connected to the processing circuitry 150 and is configured to convert input operations received from an operator into electrical signals and to output the electrical signals to the processing circuitry 150. For example, the input interface 130 is realized by using a trackball, a switch button, a mouse, a keyboard, a touch panel, and/or the like.

The display 140 is connected to the processing circuitry 150 and is configured to display various types of information and various types of image data output from the processing circuitry 150. For example, the display 140 is realized by using a liquid crystal monitor, a Cathode Ray Tube (CRT) monitor, a touch panel, or the like.

The processing circuitry 150 is configured to comprehensively control operations of the medical information processing apparatus 100. For example, the processing circuitry 150 is realized by using a processor.

An overall configuration of the medical information processing apparatus 100 according to the present embodiment has thus been explained. The medical information processing apparatus 100 according to the present embodiment structured as described above has a function of predicting a time at which treatment is to be completed on the basis of transitions up to the present time of biological index values and a treatment means for a patient undergoing the treatment.

More specifically, the processing circuitry 150 includes a first input function 151, a second input function 152, a setting function 153, a predicting function 154, a display controlling function 155, and a registering function 156. In this situation, the first input function 151 is an example of a first input unit. The second input function 152 is an example of a second input unit. The setting function 153 is an example of a setting unit. The predicting function 154 is an example of a predicting unit. The display controlling function 155 is an example of a display unit.

The first input function 151 is configured to receive an input of first transition data indicating a transition up to the present time of biological index values exhibiting conditions of a patient subject to the prediction (hereinafter "subject patient"). More specifically, when the patient ID of the subject patient is designated via the input interface 130, the first input function 151 reads the first transition data from among the diagnosis/treatment data corresponding to the patient ID and being stored in the first database 301. Further, the first input function 151 inputs the read first transition data to the predicting function 154.

The second input function 152 is configured to receive an input of second transition data expressing a transition up to the present time of the treatment means implemented on the subject patient. More specifically, when the patient ID of the subject patient is designated via the input interface 130, the second input function 152 reads the second transition data from among the diagnosis/treatment data corresponding to the patient ID and being stored in the first database 301. Further, the second input function 152 inputs the read second transition data to the predicting function 154.

The setting function 153 is configured to set a goal value of the biological index values, as a treatment index value. More specifically, when the goal biological index value is designated via the input interface 130, the setting function 153 sets the designated biological index value as the treatment index value. Although it is possible to set an arbitrary value as the treatment index value, it is desirable to set a biological index value that can be regarded as a completion of the treatment. For example, it is desirable to set a value within a normal range as the treatment index value. Further, the setting function 153 may be configured to automatically set an upper limit value or the like of the normal range of the biological index values as the treatment index value, on the basis of the type of disorder and/or biological index values of the subject patient.

On the basis of characteristics of the first transition data and the second transition data of the subject patient, the predicting function 154 is configured to predict a time (which hereinafter may be referred to as "treatment completion time") at which the biological index value of the subject patient will reach the treatment index value, on the basis of such first transition data and second transition data of one or more past patients that have characteristics similar to the characteristics of the subject patient. In this situation, the characteristics of the transition data denote characteristics of chronological changes in the transition data. In collaboration with the predicting function 154, the display controlling function 155 is configured to cause the display 140 to display a screen indicating a result predicted by the predicting function 154.

More specifically, on the basis of the characteristic of the first transition data of the subject patient and the characteristic of the second transition data of the subject patient, the predicting function 154 identifies a set made up of first transition data and second transition data having characteristics similar to the two characteristics, from the second database 302. After that, the predicting function 154 reads the first transition data in the identified set made up of the first transition data and the second transition data of the past patient and predicts a treatment completion time. In this situation, the reading of the first transition data of the past patient is performed by a method corresponding to the data structure of the second database 302.

For example, when the second database 302 stores therein the first transition data of the past patients so as to be categorized according to the types of the second transition data (the treatment means), the predicting function 154 narrows down the first transition data of the past patients to such data that is categorized in the same type of second transition data (treatment means) as that of the subject patient. Subsequently, the predicting function 154 extracts such data that has a characteristic similar to that of the first transition data of the subject patient, from among the narrowed-down first transition data.

In another example, when the second database 302 stores therein the first transition data so as to be kept in correspondence with the second transition data for the past patients, the predicting function 154 narrows down the second transition data of the past patients to such data that has a characteristic similar to the characteristic of the second transition data of the subject patient. After that, the predicting function 154 extracts such data that has a characteristic similar to the characteristic of the first transition data of the subject patient, from among the first transition data kept in correspondence with the narrowed-down second transition data.

Further, on the basis of the characteristic of the extracted first transition data of the past patient, the predicting function 154 predicts the treatment completion time at which the biological index value of the subject patient will reach the treatment index value set by the setting function 153.

When the predicting function 154 predicts the treatment completion time, for example, the display controlling function 155 displays a screen in which it is possible to compare the first transition data between the subject patient and the past patient.

Next, an example of the predicting operation of the predicting function 154 will be explained, with reference to FIG. 3. FIG. 3 is a drawing illustrating an example of the screen displayed by the display controlling function 155. In FIG. 3, the vertical axis expresses biological index values (liver function biological index values), whereas the horizontal axis expresses elapsed time since the start of the treatment. Further, the graph G1 in the solid line indicates the first transition data of the subject patient, whereas the graph G2 in the one-dot chain line indicates the first transition data of the past patient extracted by the predicting function 154. In FIG. 3, the number of extracted pieces of first transition data of past patients is 1, while the biological index value at the time of the completion of the treatment is expressed as Ve.

As explained above, the predicting function 154 extracts the first transition data of the past patient in the relationship of having a characteristic similar to the characteristic of the first transition data of the subject patient. Accordingly, the shapes of the graph G1 and the graph G2 have similarity as indicated in FIG. 3. Further, because the graph G2 represents the first transition data of the past patient whose treatment was completed, the changes in the biological index values up to the completion of the treatment are recorded.

On the basis of the changes in the biological index values indicated in the graph G2, the predicting function 154 predicts future changes to be exhibited by the first transition data of the subject patient. More specifically, the predicting function 154 predicts the future transition of the first transition data of the subject patient, by assuming that the biological index values after the most recently plotted point in time (the present time) will exhibit the same transition as the shape of the graph G2, as indicated by the broken-line graph G1a extended from the graph G1. In this situation, the method of the prediction is not particularly limited, and it is possible to use a publicly-known method such as a least squares method.

Further, on the basis of the predicted future changes in the first transition data (the broken-line graph G1a), the predicting function 154 predicts a treatment completion time. For example, when the treatment index value is Ve, the predicting function 154 derives a time T1 at which the biological index value of the subject patient will reach Ve, on the basis of the changes of the broken-line graph G1a. In this situation, the starting point of the time T1 may be the treatment start date of the subject patient or may be the point in time when the biological index value was plotted most recently (the present time).

As explained above, on the basis of the characteristics of the chronological changes in the biological index value and the treatment means of the subject patient, the predicting function 154 is configured to predict the treatment completion time, from the changes in the biological index value of the past patient that have a characteristic similar to the characteristics of the subject patient. Accordingly, for example, even when the disorder of the subject patient is a chronic disorder or a disorder caused by lifestyle, it is possible to predict the treatment completion time from the changes in the biological index value of the past patient having the similar characteristic.

Further, on the basis of the result predicted by the predicting function 154, the display controlling function 155 is configured to present the display so that it is possible to compare the changes in the biological index value of the subject patient with the changes in the biological index value of the past patient. It is therefore possible to facilitate the comparison between the biological index values, for the operator of the medical information processing apparatus 100. Further, the display controlling function 155 is configured to display the changes in the graph, up to the time when the biological index value of the subject patient predicted by the predicting function 154 reaches the treatment index value. It is therefore possible to enable the operator of the medical information processing apparatus 100 to intuitively understand the changes up to the time when the biological index value of the subject patient reaches the treatment index value.

Further, when a plurality of pieces of first transition data are extracted from the past patients, the predicting function 154 may express the extracted plurality of pieces of first transition data by using a single graph G2 similar to that in FIG. 3, by calculating a representative value, such as an average value, of the extracted plurality of pieces of first transition data. In this situation, the predicting function 154 may predict future changes in the biological index value of the subject patient on the basis of the representative value of the extracted plurality of pieces of first transition data or may predict future changes in the biological index value of the subject patient on the basis of one of the pieces of first transition data.

Further, when a plurality of pieces of first transition data are extracted from the second database 302, the predicting function 154 may derive a plurality of treatment completion times, by predicting future changes in the biological index value of the subject patient, while using each of the extracted pieces of first transition data.

FIG. 4 is a drawing illustrating another example of the screen displayed by the display controlling function 155. FIG. 4 illustrates the example of the screen corresponding to the situation where four pieces of first transition data are extracted from the past patients. The changes in the biological index value of the subject patient predicted from the pieces of first transition data are expressed by broken-line graphs G1b to G1e.

For example, of the broken-line graphs G1b to G1e, the broken-line graph G1b indicates the time T21 at which the treatment index value Ve is reached earliest, whereas the broken-line graph G1e indicates the time T24 at which the treatment index value Ve is reached latest.

As explained above, by predicting the future changes in the biological index value of the subject patient with respect to each of the pieces of first transition data extracted from the past patients, the predicting function 154 is able to present the plurality of treatment completion times at which the biological index value of the subject patient will reach the treatment index value Ve. Further, the display controlling function 155 is configured to display the changes in each prediction in a graph, up to the time when the biological index value of the subject patient reaches the treatment index value, the changes being predicted with respect to each of the pieces of first transition data extracted from the past patients. It is therefore possible to present the operator of the medical information processing apparatus 100 with the maximum value and the minimum value of the treatment completion time at which the biological index value of the subject patient will reach the treatment index value Ve, as a range.

Further, when the current treatment means is changed to another type of treatment means via the input interface 130 or the like, the predicting function 154 is configured to update the second transition data of the subject patient, by using the post-change treatment means as a treatment means to be implemented from now on. Further, by using the updated second transition data, the predicting function 154 is configured to predict a treatment completion time.

For example, when it is instructed to change the treatment means, the predicting function 154 may generate post-update second transition data, by incorporating the treatment means before and after the change into the second transition data as a treatment means to be used from now on. Alternatively, the predicting function 154 may generate post-update second transition data including only the post-change treatment means. In that situation, the post-update second transition data indicates as if the post-change treatment means had been implemented from the starting time of the treatment.

FIG. 5 is a drawing illustrating yet another example of the screen displayed by the display controlling function 155. FIG. 5 illustrates the example of the display in the situation where the currently-set treatment means is changed to another treatment means.

For example, let us discuss an example in which the treatment means up to the present time has been "walking 5,000 steps" a day, and this treatment means is changed to "walking 10,000 steps" a day. In this situation, in response to the change of the treatment means, the predicting function 154 predicts a treatment completion time on the basis of the first transition data of the past patients corresponding to the post-change treatment means.

In this situation, as illustrated in FIG. 5, the display controlling function 155 displays a broken-line graph G1g and a time T31 predicted on the basis of the pre-change treatment means; and a broken-line graph G1f and a time T32 predicted on the basis of the post-change treatment means in a distinguishable manner. Further, the display controlling function 155 displays details of the treatment means before and after the change in correspondence with the predicted treatment completion times.

As a result, the display controlling function 155 is able to enable the operator of the medical information processing apparatus 100 to recognize how much the treatment completion time changes as a result of changing the treatment means. Accordingly, because the operator of the medical information processing apparatus 100 is able to explore treatment means suitable for the conditions and preferences of the patient while changing the treatment means, the convenience is enhanced.

The registering function 156 is configured to register biological index values and the treatment means of the subject patient into the first database 301, on the basis of information input via the input interface 130 or the like.

For example, when a biological index value is acquired at every consultation, the registering function 156 registers a set made up of the biological index value acquired from the subject patient and date/time information indicating the date and time of the consultation, into diagnosis/treatment data of the subject patient (the patient ID). Further, the registering function 156 may update the first transition data of the subject patient used for predictions, by inputting the set made up of the biological index value and the date/time information to be registered, to the predicting function 154. As a result, the set made up of the biological index value and the date/time information is recorded into the diagnosis/treatment data as first transition data.

Further, when date/time information designating a specific date is input together with a biological index value, the registering function 156 registers the biological index value by using the date/time information. As a result, for example, it is possible to register a biological index value at an arbitrary point in time in the past in a retrospective manner. Further, the registering function 156 may be configured to register a treatment means in the same manner as the biological index value is registered.

Figure 6:
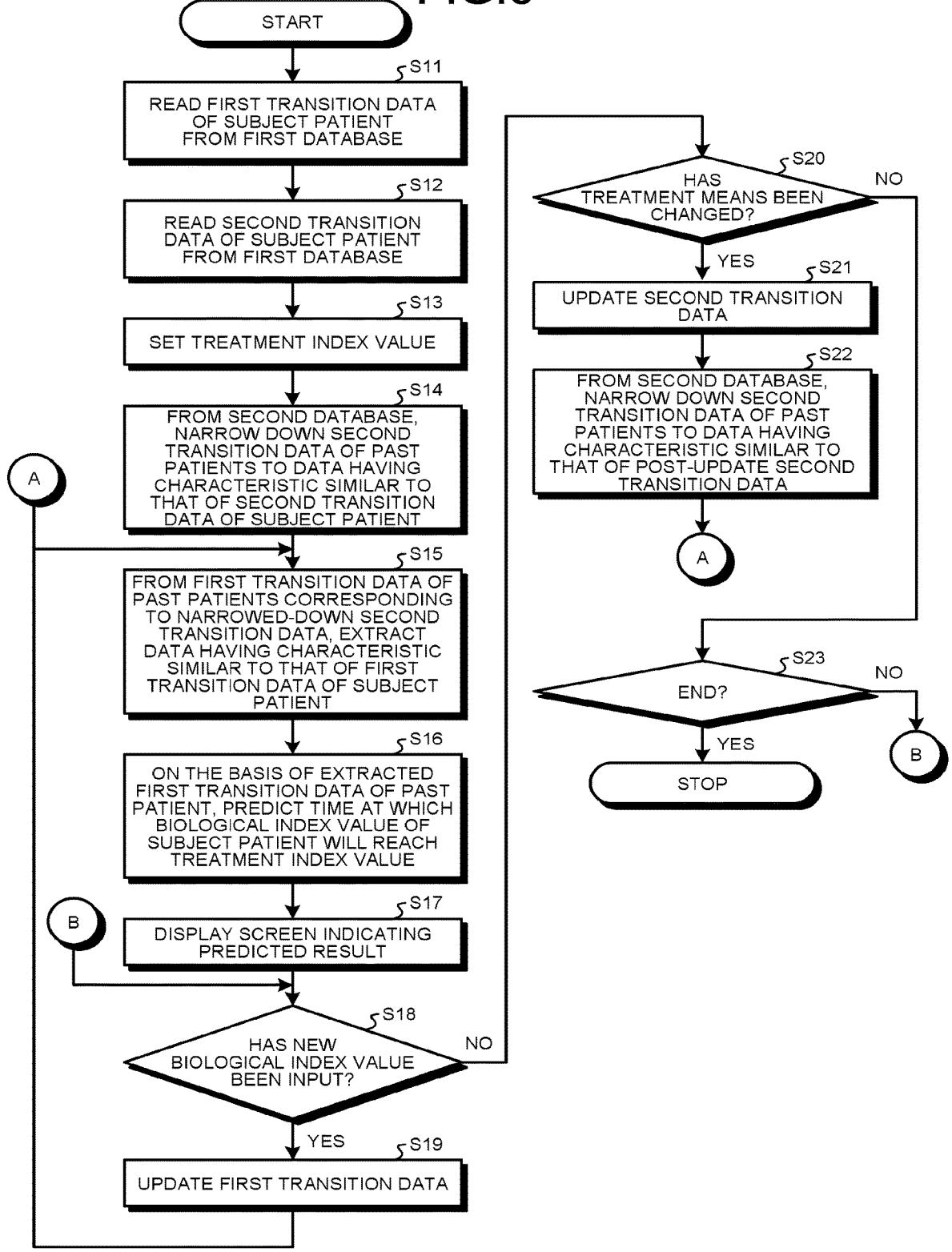
FIG. 6 is a flowchart illustrating an example of a process performed by the medical information processing apparatus according to the embodiment.

Next, an example of a process performed by the medical information processing apparatus 100 will be explained, with reference to FIG. 6. FIG. 6 is a flowchart illustrating the example of the process performed by the medical information processing apparatus 100.

When the patient ID of the subject patient is input via the input interface 130, the first input function 151 reads the first transition data of the subject patient from the first database 301 and inputs the read first transition data to the predicting function 154 (step S11). Further, the second input function 152 reads the second transition data of the subject patient from the first database 301 and inputs the read second transition data to the predicting function 154 (step S12).

Subsequently, when a goal biological index value is input via the input interface 130, the setting function 153 sets the input biological index value as a treatment index value (step S13).

From the second database 302, the predicting function 154 narrows down the second transition data of the past patients to such data that has a characteristic similar to that of the second transition data of the subject patient (step S14). Subsequently, the predicting function 154 extracts first transition data having a characteristic similar to that of the first transition data of the subject patient, from among the first transition data of the past patients corresponding to the second transition data narrowed down at step S14 (step S15).

Subsequently, on the basis of the first transition data of the past patient extracted at step S15, the predicting function 154 predicts a treatment completion time at which the biological index value of the subject patient will reach the treatment index value (step S16). Further, the display controlling function 155 causes the display 140 to display a screen indicating the result predicted by the predicting function 154 (step S17).

Subsequently, the registering function 156 judges whether or not a biological index value of the subject patient has newly been input via the input interface 130 (step S18). When a new biological index value has been input (step S18: Yes), the registering function 156 updates the first transition data by registering the input biological index value as diagnosis/treatment data of the subject patient so as to be kept in correspondence with the current date/time information (step S19), and the process proceeds to step S15.

Accordingly, the predicting function 154 re-extracts first transition data of the past patients, by using the first transition data updated at step S15. Further, on the basis of the extracted first transition data of a past patient, the process of predicting a treatment completion time is performed again. When a set made up of a biological index value and date/time information is input at step S18, the registering function 156 is configured to register the biological index value by using the input date/time information.

On the contrary, when no biological index value is input at step S18 (step S18: No), the predicting function 154 judges whether or not an instruction to change the treatment means has been input via the input interface 130 (step S20).

In this situation, when it is instructed to change the treatment means (step S20: Yes), the predicting function 154 updates the second transition data by setting the post-change treatment means as a treatment means scheduled to be implemented from now on (step S21). Subsequently, from the second database 302, the predicting function 154 narrows down the second transition data of the past patients to such data that has a characteristic similar to that of the post-change second transition data (step S22), and the process proceeds to step S15.

As a result, at step S15, the predicting function 154 extracts the data that has a characteristic similar to the characteristic of the first transition data of the subject patient, from among the first transition data of the past patients extracted by using the post-change second transition data. Further, on the basis of the extracted first transition data of the past patient, the process of predicting a treatment completion time is performed again. In this situation, the registering function 156 may perform the process of registering the post-change treatment means into the first database 301 so as to be kept in correspondence with date/time information.

Further, when it is not instructed to change the treatment means (step S20: No), the process proceeds to step S23. At step S23, the predicting function 154 judges whether or not it is instructed to end the process via the input interface 130. When it has not been instructed to end the process (step S23: No), the process returns to step S18 so that the present process is continued. On the contrary, when it is instructed to end the process (step S23: Yes), the present process is ended.

As explained above, on the basis of the characteristics of the chronological changes in the biological index value and the treatment means of the subject patient undergoing treatment, the medical information processing apparatus 100 is configured to predict the treatment completion time of the subject patient from the changes in the biological index value of the past patient having the characteristics similar to the characteristics of the subject patient. As a result, for example, even when the disorder of the subject patient is a chronic disorder or a disorder caused by lifestyle requiring long-term treatment, it is possible to efficiently predict the treatment completion time of the subject patient on the basis of the changes in the conditions up to the present time and the history of treatment means. Accordingly, because the patient undergoing the treatment is able to find out how long it will take to complete his/her treatment, it is possible to keep the patient motivated for the treatment and to thus prevent the patient from discontinuing the treatment or hospital visits.

The embodiment above may be carried out while being modified as appropriate, by altering a part of the configuration or the functions of the medical information processing apparatus 100. In the following sections, a number of modification examples of the above embodiment will be explained as other embodiments. In the following explanations, a focus will be placed on differences from the above embodiment, and detailed explanations of certain aspects that have already been explained will be omitted. Further, the modification examples described below may be carried out individually or in combination as appropriate.

First Modification Example

In the above embodiment, the example was explained in which the treatment completion time at which the biological index value of the subject patient will reach the treatment index value is predicted; however, what is predicted is not limited to this example.

For instance, when a treatment completion time is designated via the input interface 130, the predicting function 154 may predict (estimate) a treatment means capable of realizing the treatment completion time. More specifically, the predicting function 154 may be configured to predict a treatment completion time at which the biological index value of the subject patient will reach the treatment index value, with respect to each of the treatment means conditions, by making a prediction while switching among treatment means having mutually-different conditions. After that, from the predicted treatment completion times, the predicting function 154 extracts a treatment means that satisfies the designated treatment completion time.

In this situation, for example, the display controlling function 155 presents the operator of the medical information processing apparatus 100 with the treatment means capable of realizing the treatment completion time, by causing the display 140 to display the treatment means extracted by the predicting function 154. Further, the display controlling function 155 may present a display so that it is possible to compare each of the treatment means used in the prediction, with a treatment completion time derived from the treatment means.

As a result, the medical information processing apparatus 100 is able to present the operator of the medical information processing apparatus 100 with the treatment means corresponding to the designated condition for the treatment completion time. It is therefore possible to assist the work of selecting the treatment means. Further, the medical information processing apparatus 100 is also able to present the operator of the medical information processing apparatus 100 with the relationship between each of the treatment means and the treatment completion time predicted from the treatment means. It is therefore possible to efficiently assist the work of selecting the treatment means.

Second Modification Example

In the above embodiment, the example was explained in which the biological index values and the treatment means of the subject patient are obtained from the first database 301; however, possible locations to obtain the information from are not limited to this example.

For example, when the subject patient wears a portable device such as an activity monitor capable of measuring biological index values and treatment means, an arrangement is acceptable in which daily measured results are obtained from the device as biological index values and treatment means. In this situation, the first input function 151 may obtain the first transition data or the second transition data from the portable device, via an interface connectable to the portable device. Further, for example, when the results measured by the portable device are configured to be saved in a server apparatus or cloud storage, the first input function 151 may obtain the first transition data or the second transition data of the subject patient from the server apparatus or the cloud storage saving the results, via the network interface 110 or the like.

Third Modification Example

In the embodiment above, the example was explained in which the treatment completion time is predicted by using the first transition data and the second transition data of the past patients stored in the second database 302; however, possible methods for predicting the treatment completion time is not limited to this example.

As another predicting method, for example, it is also possible to predict a treatment completion time, by using a trained model that has learned, through machine learning, a relationship between characteristics of chronological changes in biological index values and treatment means and treatment completion times.

Figure 7:
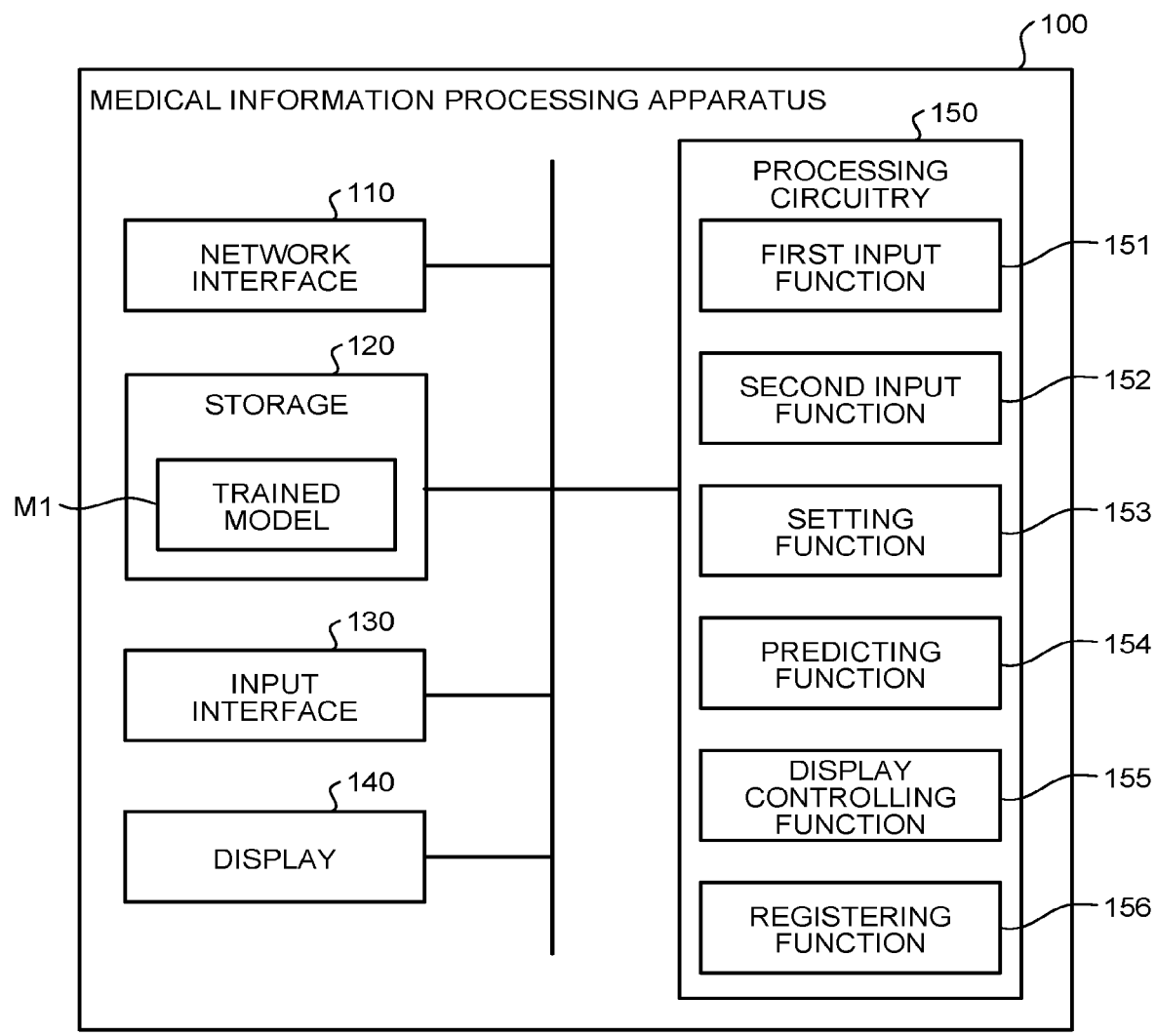
FIG. 7 is a diagram illustrating an exemplary configuration of a medical information processing apparatus according to a third modification example.

FIG. 7 is a diagram illustrating an exemplary configuration of a medical information processing apparatus 100 according to a third modification example. As illustrated in FIG. 7, the medical information processing apparatus 100 according to the present modification example has a trained model Ml stored in the storage 120.

The trained model Ml is a model of a neural network or the like generated (created) by machine-learning the first transition data and the second transition data of the past patients as training-purpose data. The trained model Ml is provided with a function to receive an input of first transition data and second transition data and to output a future transition of biological index values to be exhibited by the first transition data as an inferred result. Similarly to the embodiment above, it is assumed that a data set having a statistically significant correlation is selected as the first transition data (the biological index values) and the second transition data (the treatment means).

At the time of generating the trained model Ml, the correlation between the first transition data (the biological index values) and the second transition data (the treatment means) is machine-learned. The trained model Ml is configured so that, when the first transition data and the second transition data of a patient undergoing treatment are input thereto, a future transition to be exhibited by biological index values of the patient undergoing the treatment is output as an inferred result, on the basis of the relationship between the first transition data and the second transition data. In this situation, it is desirable to generate the trained model Ml for each of different types of disorders.

To the trained model Ml, the predicting function 154 inputs the first transition data and the second transition data of the subject patient that have been input by the first input function 151 and the second input function 152 and thereby obtains the future transition to be exhibited by the biological index values of the subject patient as the inferred result. Further, on the basis of the obtained inferred result, the predicting function 154 predicts a treatment completion time at which the biological index value of the subject patient will reach the treatment index value set by the setting function 153.

As a result, the medical information processing apparatus 100 according to the present modification example is able to achieve the same advantageous effects as those of the embodiment described above. Although FIG. 7 illustrates the example in which the medical information processing apparatus 100 stores the trained model Ml therein, possible embodiments are not limited to this example. Another apparatus such as the medical data storing apparatus 300 capable of accessing the medical information processing apparatus 100 may store the trained model Ml therein.

In the above embodiment, the example was explained in which the functional configuration of the medical information processing apparatus 100 is realized by the processing circuitry 150; however, possible embodiments are not limited to this example. For instance, in the functional configuration of the present disclosure, the functions may be realized by only hardware or by a combination of hardware and software.

The term "processor" used in the above explanations denotes, for example, a Central Processing Unit (CPU), a Graphics Processing Unit (GPU), or a circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor is configured to realize the functions by reading and executing the programs saved in the storage 120. Instead of saving the programs in the storage 120, it is also acceptable to directly incorporate the programs in the circuitry of the processor. In that situation, the processor realizes the functions by reading and executing the programs incorporated in the circuitry thereof. Further, the processor of the present embodiments does not necessarily have to be structured as a single circuit. It is also acceptable to structure one processor by combining together a plurality of independent circuits so as to realize the functions thereof.

The programs executed by the processor are provided as being incorporated, in advance, in a Read Only Memory (ROM), a storage, or the like. The programs may be provided as being recorded on a computer-readable storage medium such as a Compact Disk Read-Only Memory (CD-ROM), a Flexible Disk (FD), a Compact Disk Recordable (CD-R), Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units described above. In the actual hardware, as a result of a CPU reading and executing the programs from a storage medium such as a ROM, the modules are loaded into a main storage device and generated in the main storage device.

According to at least one aspect of the embodiments described above, it is possible to predict the treatment completion time of the patient having long-term treatment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising a processing circuitry configured:
to receive an input of first transition data indicating a transition up to a present time of a biological index value exhibiting a condition of a patient and second transition data indicating a transition up to the present time of a treatment implemented on the patient;
to set a goal value of the biological index value as a treatment index value;
to narrow down second transition data of a plurality of past patients different from the patient to second transition data of one or more of the past patients having a characteristic similar to a characteristic of the second transition data of the patient;
to extract, from first transition data of the one or more of the past patients associated with the second transition data obtained by the narrowing-down, first transition data having a characteristic similar to a characteristic of the first transition data of the patient; and
to receive an instruction for changing the treatment to be implemented on the patient;
to set the treatment after changing as a present and future treatment; and
to predict a time when the biological index value of the patient reaches the treatment index value, based on a characteristic of the second transition data of the patient, the second transition data including the present and future treatments;
wherein the processing circuitry predicts the time on a basis of a future transition of the first transition data of the patient obtained by inputting the first transition data and the second transition data of the patient to a trained model created by machine-learning using the first transition data and the second transition data of the one or more past patients and configured to receive an input of first transition data and second transition data and to output a future transition of the first transition data.

2. The medical information processing apparatus according to claim 1, wherein, when the first transition data of the patient is updated, the processing circuitry predicts the time on a basis of a characteristic of the updated first transition data.

3. The medical information processing apparatus according to claim 1, wherein
by referring to a database storing therein first transition data and second transition data of each of past patients, the processing circuitry extracts first transition data having a characteristic similar to the characteristic of the first transition data of the patient, from first transition data of one or more of the past patients having a characteristic similar to the characteristic of the second transition data of the patient, and
the processing circuitry predicts the time on a basis of the extracted first transition data.

4. The medical information processing apparatus according to claim 1, wherein
when a specific time is designated, the processing circuitry predicts the time for each of treatments having mutually-different conditions, and
the processing circuitry outputs one of the conditions of the treatments that satisfies the specific time, from among the predicted times.

5. The medical information processing apparatus according to claim 1, wherein the processing circuitry further displays the predicted time.

6. The medical information processing apparatus according to claim 5, wherein the processing circuitry displays a transition of the biological index value of the patient up to the predicted time.

7. The medical information processing apparatus according to claim 5, wherein the processing circuitry presents the display so that it is possible to compare the first transition data of the patient with the first transition data of the one or more past patients.

8. A non-transitory computer-readable storage medium comprising a plurality of computer-executable instructions that cause a computer to execute:
receiving an input of first transition data indicating a transition up to a present time of a biological index value exhibiting a condition of a patient and second transition data indicating a transition up to the present time of a treatment implemented on the patient;
setting a goal value of the biological index value as a treatment index value;
narrowing down second transition data of a plurality of past patients different from the patient to second transition data of one or more of the past patients having a characteristic similar to a characteristic of the second transition data of the patient;
extracting, from first transition data of the one or more of the past patients associated with the second transition data obtained by the narrowing-down, first transition data having a characteristic similar to a characteristic of the first transition data of the patient;
receiving an instruction for changing a treatment to be implemented on the patient;
setting the treatment after change as a present and future treatment; and
predicting a time when the biological index value of the patient reaches the treatment index value, based on a characteristic of the second transition data of the patient, the second transition data including the present and future treatments;
wherein predicting the time includes inputting the first transition data and the second transition data of the patient to a trained model created by machine-learning using the first transition data and the second transition data of the one or more past patients and receiving an input of first transition data and second transition data and outputting a future transition of the first transition data.

9. A medical information processing method comprising:
receiving an input of first transition data indicating a transition up to a present time of a biological index value exhibiting a condition of a patient and second transition data indicating a transition up to the present time of a treatment implemented on the patient;
setting a goal value of the biological index value as a treatment index value;
narrowing down second transition data of a plurality of past patients different from the patient to second transition data of one or more of the past patients having a characteristic similar to a characteristic of the second transition data of the patient;
extracting, from first transition data of the one or more of the past patients associated with the second transition data obtained by the narrowing-down, first transition data having a characteristic similar to a characteristic of the first transition data of the patient;
receiving an instruction for changing the treatment to be implemented on the patient;
setting the treatment after changing as a present and future treatment; and
predicting a time when the biological index value of the patient reaches the treatment index value, based on a characteristic of the second transition data of the patient, the second transition data including the present and future treatment;
wherein predicting the time includes inputting the first transition data and the second transition data of the patient to a trained model created by machine-learning using the first transition data and the second transition data of the one or more past patients and receiving an input of first transition data and second transition data and outputting a future transition of the first transition data.

10. A medical information processing apparatus comprising a processing circuitry configured:
to receive an input of first transition data indicating a transition up to a present time of a biological index value exhibiting a condition of a patient and second transition data indicating a transition up to the present time of a treatment implemented on the patient;
to set a goal value of the biological index value as a treatment index value;
to narrow down second transition data of a plurality of past patients different from the patient to second transition data of one or more of the past patients having a characteristic similar to a characteristic of the second transition data of the patient;
to extract, from first transition data of the one or more of the past patients associated with the second transition data obtained by the narrowing-down, first transition data having a characteristic similar to a characteristic of the first transition data of the patient; and to predict a time at which the biological index value of the patient will reach the treatment index value, on a basis of the extracted first transition data;

to receive a designation of the time;

in response to the designation of the time, to extract a condition for the treatment satisfying the designated time by predicting the time while switching treatment conditions; and to output the extracted condition for the treatment;

wherein the processing circuitry predicts the time on a basis of a future transition of the first transition data of the patient obtained by inputting the first transition data and the second transition data of the patient to a trained model created by machine-learning using the first transition data and the second transition data of the one or more past patients and configured to receive an input of first transition data and second transition data and to output a future transition of the first transition data.

11. A non-transitory computer-readable storage medium comprising a plurality of computer-executable instructions that cause a computer to execute:

receiving an input of first transition data indicating a transition up to a present time of a biological index value exhibiting a condition of a patient and second transition data indicating a transition up to the present time of a treatment implemented on the patient;

setting a goal value of the biological index value as a treatment index value;

narrowing down second transition data of a plurality of past patients different from the patient to second transition data of one or more of the past patients having a characteristic similar to a characteristic of the second transition data of the patient;

extracting, from first transition data of the one or more of the past patients associated with the second transition data obtained by the narrowing-down, first transition data having a characteristic similar to a characteristic of the first transition data of the patient; and predicting a time at which the biological index value of the patient will reach the treatment index value, on a basis of the extracted first transition data;

receiving a designation of the time;

in response to receiving the designation of the time, extracting a condition for the treatment satisfying the designated time by predicting the time while switching treatment conditions; and outputting the extracted condition for the treatment;

wherein predicting the time includes inputting the first transition data and the second transition data of the patient to a trained model created by machine-learning using the first transition data and the second transition data of the one or more past patients and receiving an input of first transition data and second transition data and outputting a future transition of the first transition data.

12. A medical information processing method comprising:

receiving an input of first transition data indicating a transition up to a present time of a biological index value exhibiting a condition of a patient and second transition data indicating a transition up to the present time of a treatment implemented on the patient;

setting a goal value of the biological index value as a treatment index value;

narrowing down second transition data of a plurality of past patients different from the patient to second transition data of one or more of the past patients having a characteristic similar to a characteristic of the second transition data of the patient;

extracting, from first transition data of the one or more of the past patients associated with the second transition data obtained by the narrowing-down, first transition data having a characteristic similar to a characteristic of the first transition data of the patient; and predicting a time at which the biological index value of the patient will reach the treatment index value, on a basis of the extracted first transition data;

receiving a designation of the time;

in response to receiving the designation of the time, extracting a condition for the treatment satisfying the designated time by predicting the time while switching treatment conditions; and outputting the extracted condition for the treatment;

wherein predicting the time includes inputting the first transition data and the second transition data of the patient to a trained model created by machine-learning using the first transition data and the second transition data of the one or more past patients and receiving an input of first transition data and second transition data and outputting a future transition of the first transition data.

* * * * *